United States Patent
Koike et al.

(10) Patent No.: US 8,265,951 B2
(45) Date of Patent: Sep. 11, 2012

(54) MEDICAL INSPECTION AID SYSTEM, MEDICAL INSPECTION AID METHOD AND COMPUTER READABLE MEDIUM

(75) Inventors: Kazumi Koike, Saitama (JP); Kunimasa Shimizu, Tokyo (JP); Takayoshi Kiuchi, Tokyo (JP); Goro Miura, Tokyo (JP); Kenji Sawada, Tokyo (JP); Koichiro Miyazaki, Tokyo (JP)

(73) Assignee: Fujifilm Corporation, Tokyo (JP)

( * ) Notice: Subject to any disclaimer, the term of this patent is extended or adjusted under 35 U.S.C. 154(b) by 319 days.

(21) Appl. No.: 12/577,122

(22) Filed: Oct. 9, 2009

(65) Prior Publication Data

US 2010/0094101 A1 Apr. 15, 2010

(30) Foreign Application Priority Data

Oct. 9, 2008 (JP) .................................. 2008-262799

(51) Int. Cl.
*G06Q 50/00* (2012.01)
(52) U.S. Cl. ........................................................ 705/2
(58) Field of Classification Search .................. 705/2, 3
See application file for complete search history.

(56) References Cited

U.S. PATENT DOCUMENTS

| 7,491,942 B2* | 2/2009 | Black et al. ............... 250/370.07 |
| 2002/0103671 A1* | 8/2002 | Pederson et al. ................... 705/2 |
| 2004/0267570 A1* | 12/2004 | Becker .............................. 705/2 |
| 2005/0197861 A1 | 9/2005 | Omori et al. |

FOREIGN PATENT DOCUMENTS

| JP | 2003-162586 A | 6/2003 |
| JP | 2005-160660 A | 6/2005 |

* cited by examiner

*Primary Examiner* — Gerald J. O'Connor
*Assistant Examiner* — Trang Nguyen
(74) *Attorney, Agent, or Firm* — McGinn IP Law Group, PLLC

(57) ABSTRACT

Adequate use item information and subject's condition criterion information are determined in advance. Actual use item information and actual subject's condition information are inputted. The actual use item information includes information of at least one used medical device and information of at least one used medicine. The actual subject's condition information indicates biological conditions of the subject after conduction of the inspection. The actual use item information is compared with the adequate use item information and the actual subject's condition information is compared with the subject's condition criterion information so that pieces of information with difference therebetween are extracted as difference information. Whether the conducted specific medical inspection was carried out adequately or not is determined based on the difference information.

22 Claims, 9 Drawing Sheets

FIG. 5

ACTUAL USE ITEM INFORMATION (MEDICAL DEVICE)

| INSPEC-TION NO. | INSPECTION DATE | SUBJECT NAME | TYPE OF INSPECTION | ENDOSCOPE WASHING HISTORY | UNIQUE NUMBER OF ENDOSCOPE | ~ |
|---|---|---|---|---|---|---|
| 1 | 2008.9.18 | ○○○○ | UPPER GAS-TROINTESTINAL ENDOSCOPY | 9.17.15:00 | XX-XXXX 001 | ~ |
| 2 | 2008.9.18 | △△△△ | UPPER GAS-TROINTESTINAL ENDOSCOPY | 9.17.16:00 | XX-XXXX 002 | ~ |
| ~ | ~ | ~ | ~ | ~ | ~ | ~ |

FIG. 6

ACTUAL USE ITEM INFORMATION (MEDICINE)

| INSPEC-TION NO. | INSPEC-TION DATE | SUBJECT NAME | TYPE OF INSPECTION | KIND AND DOSE OF MEDICINE | ~ |
|---|---|---|---|---|---|
| 1 | 2008.9.18 | ○○○○ | UPPER GASTROINTES-TINAL ENDOSCOPY | MEDICINE A 14ml | ~ |
| | | | | MEDICINE B 2g | ~ |
| | | | | MEDICINE C 4ml | ~ |
| | | | | ~ | ~ |
| ~ | ~ | ~ | ~ | ~ | ~ |

FIG. 7

ADEQUATE USE ITEM INFORMATION (MEDICAL DEVICE)

| TYPE OF INSPECTION | MEDICAL DEVICE | USE QUANTITY |
|---|---|---|
| UPPER GASTROINTESTINAL ENDOSCOPY | INDWELLING NEEDLE ○○ INDWELLING NEEDLE **-*(*) | ONE |
| | DISPOSABLE INJECTION NEEDLE --**** | ONE |
| | ~ | ~ |
| ~ | ~ | ~ |

FIG. 8

ADEQUATE USE ITEM INFORMATION (MEDICINE)

| TYPE OF INSPECTION | KIND OF PRE-TREATMENT MEDICINE | DOSE |
|---|---|---|
| UPPER GASTROINTESTINAL ENDOSCOPY | MEDICINE A | 14ml |
| | MEDICINE B | 2g |
| | MEDICINE C | 2ml |
| | MEDICINE D | 1 AMPOULE |
| | ~ | ~ |
| ~ | ~ | ~ |

FIG. 9

DIFFERENCE BETWEEN ACTUAL USE ITEM INFORMATION AND ADEQUATE USE ITEM INFORMATION AND DIFFERENCE REASON

| INSPECTION NO. | INSPECTION DATE | SUBJECT NAME | TYPE OF INSPECTION | KIND AND DOSE OF USE MEDICINE | STANDARD DOSE | DIFFERENCE REASON |
|---|---|---|---|---|---|---|
| 1 | 2008.9.18 | ○○○○ | UPPER GASTROINTESTINAL ENDOSCOPY | MEDICINE C 4ml | MEDICINE C 2ml | INCREASED DOSE BECAUSE ANESTHETIC EFFECT WAS WEAK |
| ~ | ~ | ~ | ~ | ~ | ~ | ~ |

FIG. 10

ACTUAL SUBJECT'S CONDITION INFORMATION AFTER INSPECTION

| INSPECTION NO. | INSPECTION DATE | SUBJECT NAME | TYPE OF INSPECTION | CONSCIOUSNESS CONDITION | KINESIOLOGICAL CONDITION | AUDIOVISUAL CONDITION | ~ |
|---|---|---|---|---|---|---|---|
| 1 | 2008.9.18 | ○○○○ | UPPER GASTROINTESTINAL ENDOSCOPY | NORMAL | SLIGHTLY DIZZY | NORMAL | ~ |
| ~ | ~ | ~ | ~ | ~ | ~ | ~ | ~ |

FIG. 11

SUBJECT'S CONDITION CRITERION INFORMATION AFTER INSPECTION

| TYPE OF INSPECTION | SUBJECT'S CONDITION ITEM | CRITERION |
|---|---|---|
| UPPER GASTROIN-TESTINAL ENDOSCOPY | CONSCIOUSNESS CONDITION | NORMAL (CAPABLE OF RESPONDING TO DOCTOR'S QUESTIONS) |
| | KINESIOLOGICAL CONDITION | NORMAL (NO BIG DIFFERENCE IN KINESIOLOGICAL CONDITION BETWEEN BEFORE AND AFTER INSPECTION) |
| | AUDIOVISUAL CONDITION | NORMAL (NO BIG DIFFERENCE IN AUDIOVISUAL CONDITION BETWEEN BEFORE AND AFTER INSPECTION) |
| ~ | ~ | ~ |

FIG. 12

DIFFERENCE FROM SUBJECT'S CONDITION CRITERION INFORMATION AND DIFFERENCE REASON

| IN-SPEC-TION NO. | INSPECTION DATE | SUBJECT DATE | TYPE OF INSPECTION | KINESIO-LOGICAL CONDITION | CRITERION | COMMENT ON PRE-TREATMENT DIFFERENCE REASON |
|---|---|---|---|---|---|---|
| 1 | 2008.9.18 | ○○○○ | UPPER GASTROIN-TESTINAL ENDOSCOPY | SLIGHTLY DIZZY | NORMAL (NO BIG DIFFERENCE IN KINESIO-LOGICAL CONDITION BETWEEN BEFORE AND AFTER INSPECTION) | SINCE DOSE OF MEDICINE C IS LARGE (USE 4ml WHILE 2ml IS NORMALLY USED), CONDITIONS OF SUBJECT SHOULD BE OBSERVED CONTINUOUSLY |
| ~ | ~ | ~ | ~ | ~ | ~ | ~ |

FIG. 13

```
                    INSPECTION CERTIFICATE

SUBJECT NAME:           ○○○○
INSPECTION DATE:        2008/09/18 15:00
PRE-TREATMENT STAFF:    ○○○○ NURSE
INSPECTION DOCTOR:      ○○○○ DOCTOR
TYPE OF INSPECTION:     UPPER GASTROINTESTINAL ENDOSCOPY

MEDICAL DEVICE:         ENDOSCOPE
TYPE OF USE ENDOSCOPE:  XX-XXXX
UNIQUE NUMBER:          001
WASHING HISTORY:        2008/09/17 15:00
WASHING CHEMICAL:       *****       WASHING CONDITION: EXCELLENT

INDWELLING NEEDLE:      ○○ INDWELLING NEEDLE   ONE PIECE
PRE-TREATMENT MEDICINE: *****                  14ml
....
TREATMENT:              COLORING SAMPLE   LIVING BODY MONITOR
                                          INFORMATION
SPECIMEN COLLECTION:    YES               OXYGEN DENSITY IN BLOOD: ○○
SUBJECT'S CONDITION AFTER INSPECTION:
                        EXCELLENT         BLOOD PRESSURE: ○○
POST-INSPECTION REMINDER:
```

FIG. 14

| TYPE OF INSPECTION | MEDICAL HISTORY INFORMATION | CONTRAINDICATED MEDICINE | ALTERNATIVE MEDICINE (RECOMMENDED MEDICINE TO BE USED) | DOSE OF ALTERNATIVE MEDICINE |
|---|---|---|---|---|
| UPPER GASTROINTESTINAL ENDOSCOPY | GLAUCOMA | MEDICINE D | MEDICINE E | IV |
| UPPER GASTROINTESTINAL ENDOSCOPY | DIABETES | MEDICINE D | MEDICINE E | IV |
| ~ | ~ | ~ | ~ | ~ |

FIG. 15

ADEQUATE USE ITEM INFORMATION UPDATED IN CONSIDERATION
OF CONTRAINDICATION INFORMATION (MEDICINE)

| TYPE OF INSPECTION | KIND OF PRE-TREATMENT MEDICINE | DOSE |
|---|---|---|
| UPPER GASTROINTESTINAL ENDOSCOPY | MEDICINE A | 14ml |
| | MEDICINE B | 2g |
| | MEDICINE C | 2ml |
| | MEDICINE E | 1V |
| | ~ | ~ |
| ~ | ~ | ~ |

MEDICAL INSPECTION AID SYSTEM, MEDICAL INSPECTION AID METHOD AND COMPUTER READABLE MEDIUM

CROSS-REFERENCE TO RELATED APPLICATIONS

This application is based on and claims priority under 35 USC 119 from Japanese Patent Application No. 2008-262799 filed on Oct. 9, 2008; the entire of which are incorporated herein by reference.

BACKGROUND

1. Technical Field

The present invention relates to a medical inspection aid system, a medical inspection aid method and a computer readable medium.

2. Related Art

In order to secure security and safety for a subject, it is important that an inspector and the subject can easily confirm that a medical inspection such as an endoscopy was conducted adequately. When a treatment (such as cutting a diseased region) is to be conducted in a scene where an inspection (photographing) is being conducted, there is a background-art technique which makes it possible to refer to data concerned with probability of success/failure in the treatment or difference in probability due to difference in technique. As an example of such a technique, there is an inspection management system in which conduction-completion information about conduction contents of medical practices conducted for inspections is stored so that conduction contents of a medical practice intended to be conducted from now on can be used as a key to acquire conduction-completion information corresponding to the conduction contents of the intended medical practice from the stored conduction-completion information (e.g. Patent Document 1 (JP-A-2005-160660 corresponding to US-A-2005/0197861)). In addition, there is a medical information distribution system in which a plurality of pieces of medical information with respect to a subject have been stored in advance and these plurality of pieces of medical information are transmitted to the patient's side through a portable terminal so that the patient side can easily check a postoperative result, postoperative care, dosage time, etc. (e.g. Patent Document 2 (JP-A-2003-162586)).

However, by either of these methods, a subject per se, an inspector or the like cannot easily check whether a medical inspection such as an endoscopy was conducted on the subject adequately or not.

SUMMARY

An illustrative object of the invention is to provide a medical inspection aid system, a medical inspection aid method and a computer readable medium in which it is possible to easily and surely recognize whether a medical inspection was carried out adequately or not, from information about presence/absence of conduction of predetermined events before and after the medical inspection, difference between before and after the inspection, a reason for the difference, etc.

(1) According to an aspect of the invention, a medical inspection aid system for determining whether a medical inspection conducted on a subject was carried out adequately or not, includes: an information input unit which inputs actual use item information and actual subject's condition information, the actual use item information including information of at least one medical device used in a specific medical inspection conducted on a subject and information of at least one medical device and medicine used in a pre-treatment carried out on the subject prior to the specific medical inspection, the actual subject's condition information indicating biological conditions of the subject after conduction of the specific medical inspection; an information storage unit which stores the input information from the information input unit, adequate use item information and subject's condition criterion information, the adequate use item information including information of at least one normal medical device to be used in the medical inspection and at least one normal medical device and medicine to be used in the pre-treatment, the subject's condition criterion information indicating criteria for determining whether the biological conditions of the subject are normal or not after conduction of the medical inspection; a difference information extraction unit which compares the actual use item information with the adequate use item information and compares the actual subject's condition information with the subject's condition criterion information to thereby extract differences therebetween as difference information; and an adequacy determination unit which determines whether the conducted specific medical inspection was carried out adequately or not, based on the difference information.

According to the medical inspection aid system, actual use item information and actual subject's condition information in a medical inspection are compared with normal standard information so that whether the conducted medical inspection was carried out adequately or not can be determined.

(2) According to the medical inspection aid system of (1), the difference information extraction unit may compare the actual use item information with the adequate use item information to extract information of at least one medical device and medicine with differences therebetween, and registers the extracted information as use item difference data in the information storage unit. The difference information extraction unit may also compares the actual subject's condition information with the subject's condition criterion information to thereby extract information of biological conditions where at least one of the actual subject's conditions fails to meet a corresponding one of the criteria, and registers the extracted information as biological condition difference data in the information storage unit. And when there is no registration of the difference information including the use item difference data and the biological condition difference data registered by the difference information extraction unit, the adequacy determination unit may determine that the conducted specific medical inspection was conducted adequately.

According to the medical inspection aid system, use item difference information and biological condition difference data are included in difference information and whether a medical inspection was adequate or not can be determined based on presence/absence of registration of these data.

(3) According to the medical inspection aid system of (2), each of the actual use item information and the adequate use item information may include information of names of use items and quantities of the use items. And when difference in at least one of a name of each use item and a quantity of the use item is recognized between the actual use item information and the adequate use item information, data of the use item with the recognized difference may be registered as use item difference data in the information storage unit.

According to the medical inspection aid system, when difference in at least one of a name of a use item and a quantity of the use item is recognized, difference data of the use item are registered as use item difference data in the information storage unit.

(4) The medical inspection aid system of (2) or (3), may further include: a difference reason adding unit which registers a reason for difference of the registered difference data in the information storage unit when one of the use item difference data and the biological condition difference data is registered in the information storage unit. the adequacy determination unit may remove difference data from the difference information when the reason is registered for the difference data by the difference reason adding unit.

According to the medical inspection aid system, even if difference information is present, the difference information is removed when a reason for the difference is registered for the difference information. The difference information can be regarded as absent. Thus, there is no fear that it is concluded due to the difference information that a medical inspection was not adequate.

(5) The medical inspection aid system of any of (1) through (4), may further include a contraindicated combination avoidance unit. The information storage unit may store subject's medical condition information, contraindicated combination information and alternative combination information, the subject's medical condition information indicating disorders and symptoms of the subject, the contraindicated combination information indicating contraindicated combinations of the medical devices and the medicines with respect to the subject's medical condition information, the alternative combination information indicating alternative combinations for avoiding the contraindicated combinations. When a contraindicated combination with the subject's medical condition information is found in the adequate use item information, the contraindicated combination avoidance unit may change the contraindicated combination to a corresponding one of the alternative combinations based on the contraindicated combination information and the alternative combination information.

According to the medical inspection aid system, when a contraindicated combination of a medical device and a medicine was found with reference to subject's medical condition information, the contraindicated combination can be changed to an alternative combination.

(6) According to the medical inspection aid system of any one of (1) through (5), the information storage unit may store pieces of the adequate use item information and pieces of the subject's condition criterion information in accordance with a plurality of medical inspections respectively. And the difference information extraction unit may selectively use one piece of the adequate use item information and one piece of the subject's condition criterion information corresponding to the medical inspection conducted on the subject.

According to the medical inspection aid system, individual pieces of adequate use item information and the subject's condition criterion information are used in accordance with a plurality of kinds of medical inspections so that general-purpose properties can be enhanced.

(7) The medical inspection aid system of any one of (1) through (6), may further include: an inspection certificate creation unit which creates an inspection certificate when the adequacy determination unit concludes that the conducted specific medical inspection was adequate.

According to the medical inspection aid system, an inspection certificate is created so that it is possible to certify that the medical inspection was carried out adequately.

(8) According to the medical inspection aid system of (7), the inspection certificate may include at least the actual use item information and the actual subject's condition information corresponding to the specific medical inspection.

According to the medical inspection aid system, actual use item information and actual subject's condition information are included in an inspection certificate so that specific grounds that the medical inspection was carried out adequately can be described explicitly to thereby improve reliability of the medical inspection.

(9) According to the medical inspection aid system of (7) or (8), the information storage unit may store post-inspection reminder information for the subject after conduction of the specific medical inspection. And the inspection certificate may include the post-inspection reminder information.

According to the medical inspection aid system, post-inspection reminder information is included in an inspection certificate so that a subject, subject's family or the like can be informed of, for example, information of things to pay attention to about the subject after the inspection, such as timing of dosing prescribed medicines including medicines taken orally, restricted things in daily life, etc.

(10) The medical inspection aid system of any one of (7) through (9), may further include: a print output unit which prints the inspection certificate.

According to the medical inspection aid system, an inspection certificate can be printed so that it is possible to check the inspection certificate on a print easily without any display medium.

(11) The medical inspection aid system of any one of (1) through (10), may further include: a display unit which displays the difference information on a monitor screen together with any one of the information stored in the information storage unit.

According to the medical inspection aid system, difference information and other information can be displayed on a monitor screen so that difference from contents of a general adequate medical inspection can be grasped quickly and accurately.

(12) According to another aspect of the invention, a medical inspection aid method for determining whether a medical inspection conducted on a subject was carried out adequately or not, includes: determining adequate use item information and subject's condition criterion information in advance, the adequate use item information including information of at least one normal medical device to be used in a medical inspection and information of at least one normal medical device and medicine to be used in a pre-treatment to be conducted prior to the medical inspection, the subject's condition criterion information indicating criteria for determining whether biological conditions of the subject are normal or not after conduction of the medical inspection; inputting actual use item information and actual subject's condition information, the actual use item information including information of at least one medical device used in the specific medical inspection conducted on the subject and information of at least one medical device and medicine used in the pre-treatment, the actual subject's condition information indicating biological conditions of the subject after conduction of the specific medical inspection; comparing the actual use item information with the adequate use item information and comparing the actual subject's condition information with the subject's condition criterion information to thereby extract differences therebetween as difference information; and determining whether the conducted specific medical inspection was carried out adequately or not, based on the extracted difference information.

(13) The medical inspection aid method defined in the paragraph (12), may further include: comparing the actual use item information with the adequate use item information to extract information of at least one medical device and medicine with differences therebetween, and registering the extracted information as use item difference data; comparing the actual subject's condition information with the subject's condition criterion information to thereby extract information of biological conditions where at least one of the actual subject's conditions fails to meet a corresponding one of the criteria, and registering the extracted information as biological condition difference data; and determining that the conducted specific medical inspection was carried out adequately when there is no registration of the difference information including the use item difference data and the biological condition difference data.

(14) According to the medical inspection aid method of (13), each of the actual use item information and the adequate use item information may include information of names of use items and quantities of the use items. And when difference in at least one of a name of each use item and a quantity of the use item is recognized between the actual use item information and the adequate use item information, data of the use item with the recognized difference may be registered as use item difference data.

(15) The medical inspection aid method of (13) or (14), may further include: removing difference data from the difference information registered as one of the use item difference data and the biological condition difference data when a reason of difference occurring in the difference data is registered for the difference data.

(16) The medical inspection aid method of any one of (12) through (15), may further include: changing a contraindicated combination to a corresponding one of alternative combinations based on subject's medical condition information, contraindicated combination information and alternative combination information when the contraindicated combination with the subject's medical condition information is found in the adequate use item information, the subject's medical condition information indicating disorders and symptoms of the subject, the contraindicated combination information indicating contraindicated combinations of the medical devices and the medicines with respect to the subject's medical condition information, the alternative combination information indicating alternative combinations to the contraindicated combinations.

(17) The medical inspection aid method of any one of (12) through (16), may further include: selectively using one piece of the adequate use item information and one piece of the subject's condition criterion information corresponding to the medical inspection conducted on the subject, from pieces of the adequate use item information and pieces of the subject's condition criterion information prepared in advance in accordance with a plurality of types of medical inspections.

(18) The medical inspection aid method of any one of the paragraphs (12) through (17), may further include: creating an inspection certificate when it is concluded that the conducted specific medical inspection was adequate.

(19) According to the medical inspection aid method of (18), the inspection certificate may include at least the actual use item information and the actual subject's condition information corresponding to the conducted specific medical inspection.

(20) According to the medical inspection aid method of (18) or (19), the inspection certificate may include post-inspection reminder information for the subject after conduction of the specific medical inspection.

(21) The medical inspection aid method of any one of (18) through (20), may further include: printing out the inspection certificate after the inspection certificate is created.

(22) The medical inspection aid method of any one of (12) through (21), may further include: displaying the difference information on a monitor screen together with at least one of the actual use item information and the actual subject's condition information.

According to any one of the aforementioned medical inspection aid methods, actual use item information and actual subject's condition information in a medical inspection are compared with normal standard information so that it is possible to determine whether the conducted medical inspection was carried out adequately or not.

(23) According to another aspect of the invention, a computer readable medium storing a program causing a computer to execute a process for a medical inspection aid method for determining whether a medical inspection conducted on a subject was carried out adequately or not, the process comprising: determining adequate use item information and subject's condition criterion information in advance, the adequate use item information including information of at least one normal medical device to be used in a medical inspection and information of at least one normal medical device and medicine to be used in a pre-treatment to be conducted prior to the medical inspection, the subject's condition criterion information indicating criteria for determining whether biological conditions of the subject are normal or not after conduction of the medical inspection; inputting actual use item information and actual subject's condition information, the actual use item information including information of at least one medical device used in the specific medical inspection conducted on the subject and information of at least one medical device and medicine used in the pre-treatment, the actual subject's condition information indicating biological conditions of the subject after conduction of the specific medical inspection; comparing the actual use item information with the adequate use item information and comparing the actual subject's condition information with the subject's condition criterion information to thereby extract differences therebetween as difference information; and determining whether the conducted specific medical inspection was carried out adequately or not, based on the extracted difference information.

(24) According to the computer readable medium of (23), the process may further include: comparing the actual use item information with the adequate use item information to extract information of at least one medical device and medicine with differences therebetween, and registering the extracted information as use item difference data; comparing the actual subject's condition information with the subject's condition criterion information to thereby extract information of biological conditions where at least one of the actual subject's conditions fails to meet a corresponding one of the criteria, and registering the extracted information as biological condition difference data; and determining that the conducted specific medical inspection was carried out adequately when there is no registration of the difference information including the use item difference data and the biological condition difference data.

(25) According to the computer readable medium of (24), each of the actual use item information and the adequate use item information may include information of names of use items and quantities of the use items. And when difference in at least one of a name of each use item and a quantity of the use item is recognized between the actual use item information and the adequate use item information, data of the use item with the recognized difference may be registered as use item difference data.

(26) According to the computer readable medium of (24) or (25), the process may further include: removing difference data from the difference information registered as one of the use item difference data and the biological condition difference data when a reason of difference occurring in the difference data is registered for the difference data.

(27) According to the computer readable medium of any of (23) through (26), the process may further include: changing a contraindicated combination to a corresponding one of alternative combinations based on subject's medical condition information, contraindicated combination information and alternative combination information when the contraindicated combination with the subject's medical condition information is found in the adequate use item information, the subject's medical condition information indicating disorders and symptoms of the subject, the contraindicated combination information indicating contraindicated combinations of the medical devices and the medicines with respect to the subject's medical condition information, the alternative combination information indicating alternative combinations to the contraindicated combinations.

(28) According to the computer readable medium of any of (23) through (27), the process may further include: selectively using one piece of the adequate use item information and one piece of the subject's condition criterion information corresponding to the medical inspection conducted on the subject, from pieces of the adequate use item information and pieces of the subject's condition criterion information prepared in advance in accordance with a plurality of types of medical inspections.

(29) According to the computer readable medium of any of (23) through (28), the process may further include: creating an inspection certificate when it is concluded that the conducted specific medical inspection was adequate.

(30) According to the computer readable medium of (29), the inspection certificate may include at least the actual use item information and the actual subject's condition information corresponding to the conducted specific medical inspection.

(31) According to the computer readable medium of (29) or (30), the inspection certificate may include post-inspection reminder information for the subject after conduction of the specific medical inspection.

(32) According to the computer readable medium of any one of (29) through (31), the process may further include: printing out the inspection certificate after the inspection certificate is created.

(33) The computer readable medium of any one of (23) through (32), the process may further include: displaying the difference information on a monitor screen together with at least one of the actual use item information and the actual subject's condition information.

According to any one of the aforementioned computer readable mediums, a computer can aid in comparing actual use item information and actual subject's condition information in a medical inspection with normal standard information so as to determine whether the conducted medical inspection was carried out adequately or not.

With the configurations of any of (1) through (33), an inspector conducting a medical inspection and a subject suffering the medical inspection can easily and surely recognize that the medical inspection was carried out adequately.

BRIEF DESCRIPTION OF THE DRAWINGS

FIG. 5 is a table showing information of used medical devices as actual use item information.

FIG. 6 is a table showing information of used medicines as actual use item information.

FIG. 7 is a table showing information of normal medical devices to be used in a medical inspection, as adequate use item information.

FIG. 8 is a table showing information of normal medicines used in the medical inspection, as adequate use item information.

FIG. 9 is a table showing difference information between the actual use item information and the adequate use item information.

FIG. 10 is a table showing actual subject's condition information after the inspection.

FIG. 11 is a table showing subject's condition criterion information.

FIG. 12 is a table showing difference information between the actual subject's condition information after the inspection and the subject's condition criterion information.

FIG. 13 is a view showing an example of an inspection certificate.

FIG. 14 is a table showing contraindicated combination information as contraindication information and alternative combination information.

FIG. 15 is a table showing a result of the adequate use item information updated in consideration of the contraindication information.

DETAILED DESCRIPTION

A medical inspection aid system will be described below in detail with reference to the drawings.

Figure 1:
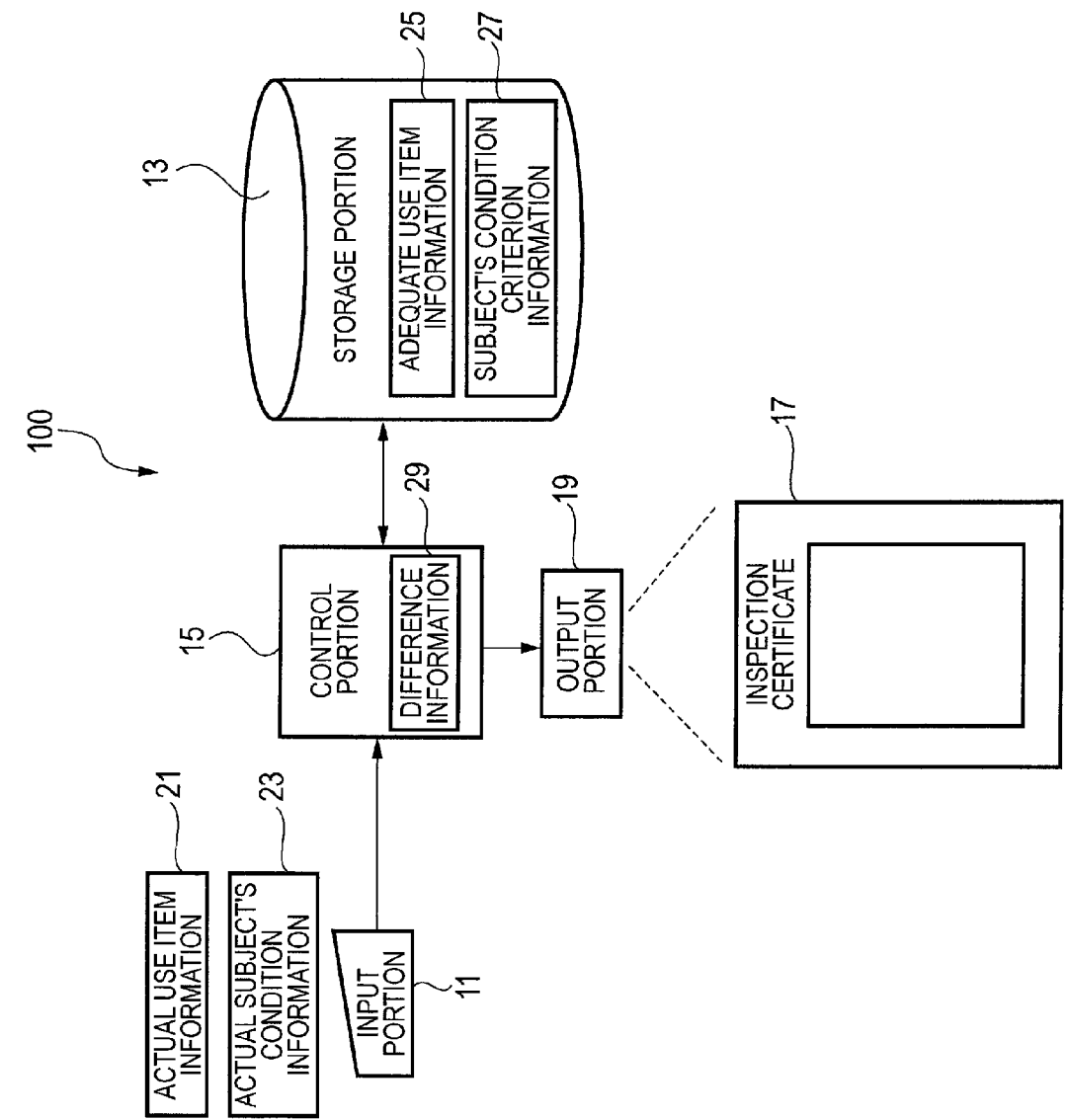
FIG. 1 is a schematic block configuration diagram of a medical inspection aid system for explaining an exemplary embodiment of the invention.

FIG. 1 is a schematic block configuration diagram of a medical inspection aid system for explaining an exemplary embodiment of the invention.

A medical inspection aid system 100 serves to determine whether a medical inspection conducted on a subject was carried out adequately or not. The medical inspection aid system 100 includes an input portion 11, a storage portion 13, a control portion 15, and an output portion 19 as main constituent elements. The input portion 11 serves as an information input unit. The storage portion 13 serves as an information storage unit. The control portion 15 controls the respective portions overall and determines whether a medical inspection was carried out adequately or not. The output portion 19 outputs an inspection certificate 17 when the medical inspection was carried out adequately. Incidentally, although an endoscopy is described here by way of example, the type of the medical inspection is not limited thereto.

The input portion 11 inputs actual use item information 21 and actual subject's condition information 23. The actual use item information 21 includes information of medical devices such as an endoscope used for conducting a specific medical inspection such as an endoscopy on a subject, and information of medical devices and medicines such as an injection needle used in a pre-treatment conducted prior to the specific medical inspection. The actual subject's condition information 23 expresses biological conditions of the subject after conduction of the specific medical inspection.

Here, the information of medical devices means information about use materials such as the endoscope, the injection needle, a catheter and a stent, model names or unique numbers (if reuse items such as an endoscope) of the use materials, and use quantities of the use materials. In addition, the information of medicines means commercial medicine names (product names) or ingredient names, dosages, etc. Here, although commercial medicine names which are commonly called are used as the information of medicines, the invention is not limited thereto.

The storage portion 13 stores the input information from the input portion 11, adequate use item information 25 and subject's condition criterion information 27. The adequate use item information 25 includes information of normal medical devices to be used in the medical inspection and information of normal medicines to be used in the pre-treatment. The subject's condition criterion information 27 expresses criteria for determining whether biological conditions of the subject are normal or not after conduction of the medical inspection.

The control portion 15 serves as a difference information extraction unit and an adequacy determination unit. As the difference information extraction unit, the control portion 15 compares the actual use item information 21 with the adequate use item information 25, and compares the actual subject's condition information 23 with the subject's condition criterion information 27 to thereby extract differences therebetween as difference information 29. As the adequacy determination unit, the control portion 15 determines whether the conducted specific medical inspection was carried out adequately or not, based on the difference information 29. The difference information 29 means information about presence/absence of conduction of predetermined events before and after the medical inspection, difference of the conduction contents, difference of the biological conditions before and after the medical inspection, a reason for the difference, etc.

Figure 2:
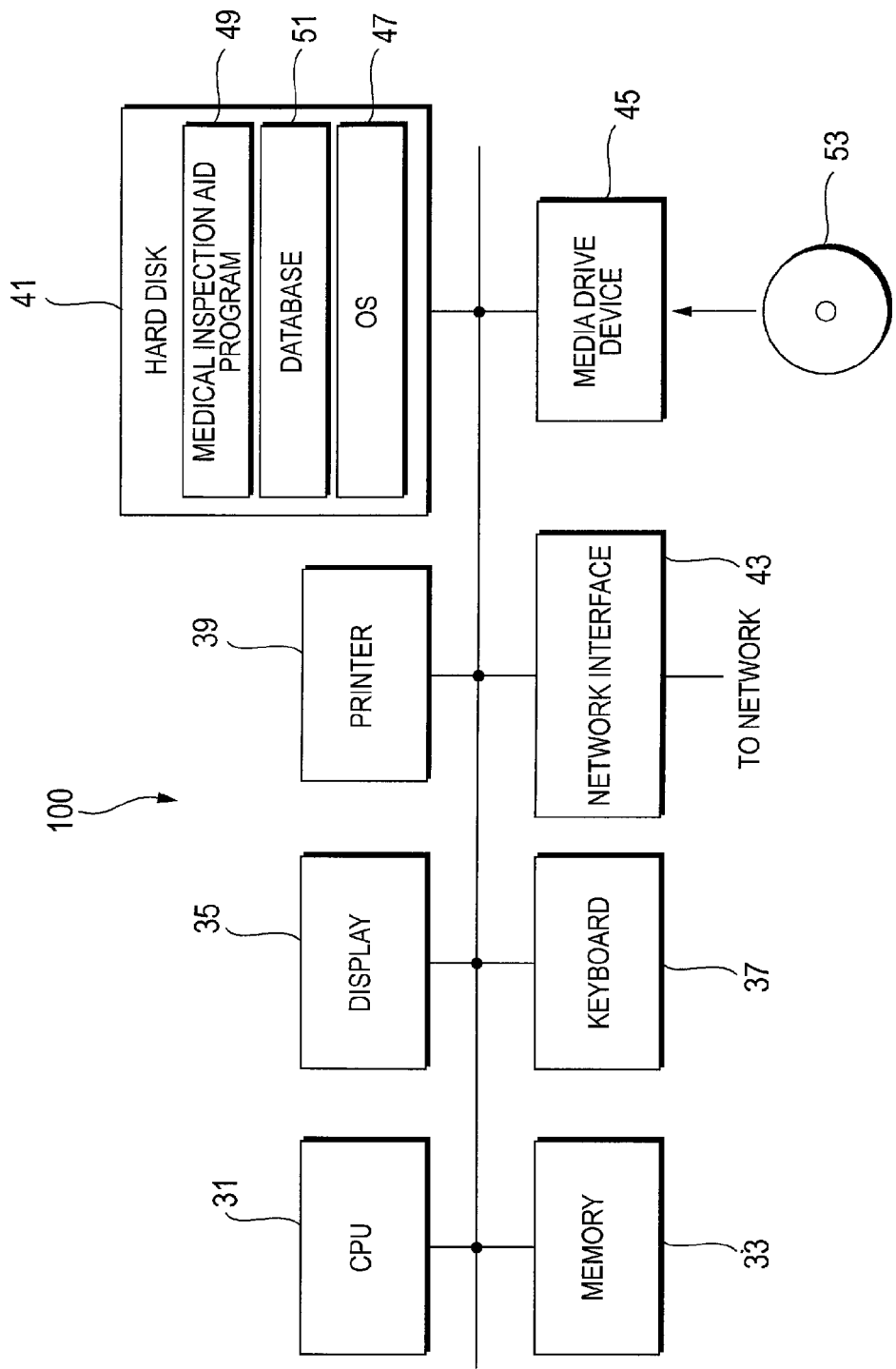
FIG. 2 is a hardware configuration diagram in the case where the medical inspection aid system shown in FIG. 1 is implemented by use of a CPU.

FIG. 2 shows a hardware configuration diagram when the medical inspection aid system shown in FIG. 1 is implemented by use of a CPU.

In FIG. 2, a memory 33, a display 35, a keyboard 37, a printer 39, a hard disk 41, and a media drive device 45 are connected to the CPU 31. The display 35 serves as a display unit. The keyboard (also including other input devices such as a mouse, one-dimensional and two-dimensional code readers, and a wireless communication input instrument) 37 serves as an information input unit. The printer 39 serves as a print output unit. An example of the media drive device 45 includes a CD-ROM drive. These elements may be formed into a network through a network interface 43.

An operating system (OS) 47, a medical inspection aid program 49 and a database 51 are stored in the hard disk 41. The medical inspection aid program 49 makes the computer execute a medical inspection aid method which will be described later. The database 51 is used for the medical inspection aid program 49. For example, at least parts of the medical inspection aid program 49 and the database 51 are installed into the hard disk 41 through a recording medium 53 by the media drive device 45. It is a matter of course that at least part of the medical inspection aid program 49 and the database 45 may be installed into the hard disk 41 through the network.

Information input from the keyboard 37, information stored in the memory 33, the hard disk 41 and the media drive device 45, various kinds of information input from the network, etc. can be displayed on the display 35.

Here, an aid method carried out by the medical inspection aid system 100 will be described schematically and simply with reference to FIG. 3.

Figure 3:
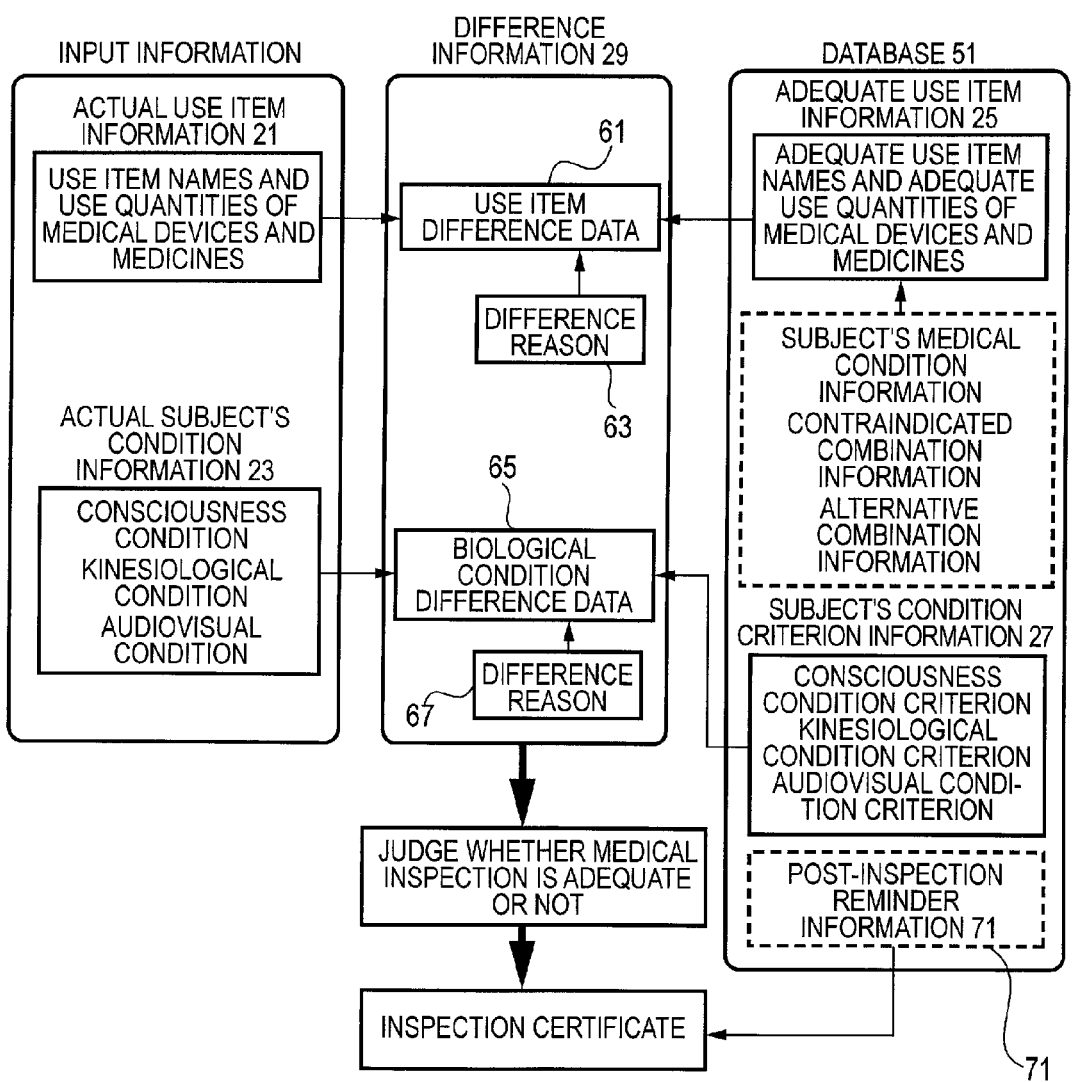
FIG. 3 is a block diagram showing various kinds of information for explaining a medical inspection judgment method performed by the medical inspection aid system.

FIG. 3 is a block diagram showing various kinds of information for explaining a medical inspection determination method carried out by the medical inspection aid system.

First, as input information, the actual use item information 21 is information about medical devices used for conducting a specific medical inspection on a subject. The actual use item information 21 includes the model type or unique number of an endoscope which was actually used for the subject, the washing date of the used endoscope, etc. In addition, the actual use item information 21 includes information of medical devices and medicines actually used in a pre-treatment conducted prior to the specific medical inspection, such as an injection needle for preliminarily giving a dose of an anesthetic or an analgesic before insertion of the endoscope into the subject, medicine names and doses of the medicines, etc. These pieces of actual use item information 21 are input after the medical inspection was conducted on the subject.

On the other hand, the database 51 stored in the hard disk 41 (see FIG. 2) contains the adequate use item information 25 including information of normal medical devices to be used in various medical inspections and information of normal medical devices and medicines to be used in pre-treatments for those medical inspections. The normal medical devices mean standard medical devices which should be normally used in the medical inspections. The normal medicines mean standard medicines which should be normally used in the pre-treatments. Data about adequate use item names and adequate use quantities of these normal medical devices and medicines are included in the adequate use item information 25. The adequate use item information 25 is compared with the actual use item information 21 actually used in the medical inspection, to thereby check whether there is any difference in medical device or medicine therebetween or not. Specifically, the actual use item information 21 is compared with the adequate use item information 25, so that information of difference in medical devices and medicines is extracted as use item difference data 61.

Presence of the use item difference data 61 means that the use item in the conducted medical inspection is different from a use item in a normally conducted medical inspection. However, there may occur a case where the use item normally used is equivalent to a contraindicated item in accordance with the medical conditions of the subject, or the like. When there is such a contraindicated combination, the contraindicated combination is changed to an alternative combination which will not become a contraindicated combination. In such a case, if the combination is determined not to be adequate due to the difference, the determination would be wrong. Therefore, a difference reason 63 is registered for the use item difference data 61 containing a difference and the use item difference data 61 with the registered reason is removed from the difference information 29. As will be described in detail later, data removed from the difference information 29 can be regarded as data with no difference.

Next, as input information, the actual subject's condition information 23 is information of biological conditions of the subject, such as consciousness condition, kinesiological condition and audiovisual condition of the subject after a medical inspection such as an endoscopy. For example, the actual subject's condition information 23 includes information as to "whether the subject felt dizzy or not" and "whether the subject could respond to questions or not". These pieces of actual subject's condition information 23 are input after the medical inspection was conducted on the subject.

On the other hand, the subject's condition criterion information 27 expressing criteria for judging whether biological conditions of the subject are normal or not after conduction of various medical inspections is contained in the database 51 stored in the hard disk 41 (see FIG. 2). The criteria for judging whether biological conditions of the subject are normal or not mean criteria for judging whether the subject is in normal conditions or not after conduction of a medical inspection in question. That is, the criteria include data with which a nurse, a doctor, or the like who has conducted a pre-treatment or a medical inspection on a subject can check and decide the conditions of the subject. Data of these criteria are contained in the subject's condition criterion information 27. The subject's condition criterion information 27 is compared with the actual subject's condition information 23, so that whether there is a difference in biological conditions therebetween or not can be checked. Specifically, when the actual subject's condition information 23 is compared with the subject's condition criterion information 27, the actual subject's condition information may include a piece of information of a biological condition in which an actual subject's condition fails to meet a corresponding criterion. In this case, the piece of information is extracted as biological condition difference data 65.

Also in this case, presence of the biological condition difference data 65 means that some symptom after the conducted medical inspection is different from that after a normally conducted medical inspection. Due to the difference, the medical inspection would be determined not to be adequate. However, the determination will be wrong if the subject can be recovered by an adequate treatment corresponding to the symptom of the subject. Therefore, a difference reason 67 is registered in the biological condition difference data 65 for the difference and the biological condition difference data 65 with the registered reason is removed from the difference information 29.

When there is no registration of the use item difference data 61 and the biological condition difference data 65 in the difference information 29, the control portion 15 (see FIG. 1) determines that the conducted specific medical inspection was carried out adequately. Here, the control portion 15 serves as a difference information extraction unit and an adequacy determination unit. Further, in the case where there is difference information 29, the control portion 15 also serves as a difference reason adding unit to register the difference reasons 63 and 67 in the database 51 for the difference information 29.

When the medical inspection is determined to be adequate, the control portion 15 issues an inspection certificate including at least the actual use item information 21 and the actual subject's condition information 23.

According to the medical inspection aid method described above, it can be known that the conducted medical inspection was conducted by use of the adequate use items and it can be also known that the biological conditions after the conducted medical inspection were normal. The medical inspection is not limited to one type of medical inspection. Adequate use item information 25 and subject's condition criterion information 27 may be prepared in advance for each of a plurality of types of medical inspections. When the actual use item information 21 and the actual subject's condition information 23 are compared with the adequate use item information 25 and the subject's condition criterion information 27, whether any one of the medical inspections was conducted adequately or not can be determined in the same manner. Thus, it is possible to increase general-purpose properties of the medical inspection aid system.

Then, the medical inspection aid method will be described in detail based on a more specific example.

Figure 4:
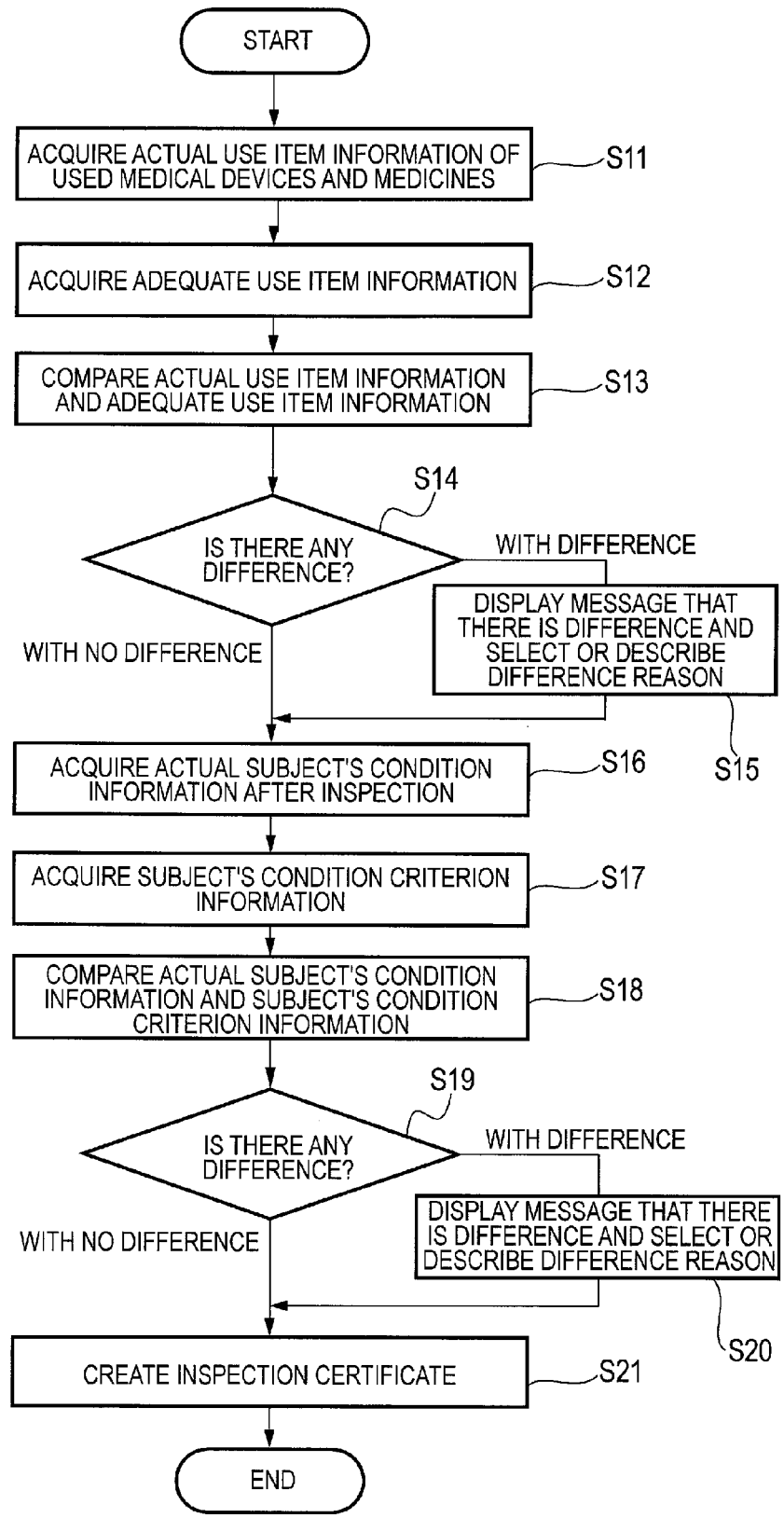
FIG. 4 is a flow chart showing a procedure up to creation of an inspection certificate, performed by the medical inspection aid method.

FIG. 4 shows a procedure up to creation of an inspection certificate, carried out by the medical inspection aid method.

First, actual use item information of used medical devices and used medicines is acquired (S11). FIG. 5 shows information of used medical devices as the actual use item information. FIG. 6 shows information of used medicines as the actual use item information. Pieces of the information of medical devices shown in FIG. 5 are grouped under ordered medical inspections (1, 2 . . . ). Here, the information of medical devices includes the conduction date of a medical inspection, the name of a subject, the type of the inspection, use information of a medical device such as the type and washing history of an inspection machine such as an endoscope etc., and information of a medical device such as an injection needle used in a pre-treatment. The type of the inspection may include an upper gastrointestinal endoscopy or a lower gastrointestinal endoscopy. On the other hand, the information of used medicines includes information about the conduction date of the inspection, the name of the subject, the type of the inspection, kinds and quantities of used medicines, etc. These pieces of information are inputted from the keyboard 37, the network interface 43, the media drive device 45 and the input portion 11 shown in FIG. 2, and stored in the database 51 of the hard disk 41, the memory 33, etc.

Then, adequate use item information is acquired by the memory 33 (S12). FIG. 7 shows information of normal medical devices to be used in medical inspections as the adequate use item information. FIG. 8 shows information of normal medicines to be used in the medical inspections as the adequate use item information. The information of normal medical devices includes information about a medical device, a use quantity of the medical device, etc. in accordance with each type of inspection. On the other hand, the information of normal medicines includes information about kinds, doses, etc. of medicines to be used in a pre-treatment in accordance with each type of inspection. These pieces of adequate use item information are registered in advance in the database 51 shown in FIG. 2.

After the actual use item information and the adequate use item information have been inputted, these pieces of information are compared with each other (S13). In the embodiment, there is difference between the actual use item information (medicine) in FIG. 6 and the adequate use item information (medicine) in FIG. 8 (S14). That is, the standard dose of a medicine C is 2 ml whereas the actually used dose of the medicine C is 4 ml. In this case, a message indicating presence of use item difference data 61 (see FIG. 3) is displayed and a reason for the difference is selected or described (S15). That is, a message indicating that difference is found in the medicine C is displayed on the display 35 (FIG. 2) and a reason for the difference is inputted in accordance with necessity. Examples of methods of inputting the reason include a method of selectively designating suitable one from a plurality of reasons displayed on the display 35 (e.g. selecting one from a pull-down menu) and a method of directly inputting the reason by means of the keyboard 37 etc. FIG. 9 shows such information with difference by way of example. In FIG. 9, the actually used dose of the medicine C is larger than the standard dose of the medicine C, but a reason is described that the dose was increased because the anesthetic effect was weak. These pieces of information are displayed on the display 35 so as to be checked easily. That is, difference from the contents of the general adequate medical inspection can be grasped quickly and accurately.

In the case where a reason is described for difference between the actual use item information and the adequate use item information as described above or in the case where there is no difference therebetween, information of actual conditions of the subject after the inspection is then acquired (S16). FIG. 10 shows the actual subject's condition information after the inspection. The actual condition information includes consciousness condition, kinesiological condition, audiovisual condition, etc. of the subject in accordance with each inspection number. Here, there is shown a result that the consciousness condition and the audiovisual condition were normal but the kinesiological condition involved a slightly dizzy one.

Then, subject's condition criterion information is acquired by the memory 33 (S17). The subject's condition criterion information is data in which biological conditions of the subject and criteria for judging the biological conditions are defined in accordance with each type of inspection, as shown in FIG. 11. For example, consciousness condition, kinesiological condition and audiovisual condition are defined in an upper gastrointestinal endoscopy. The criterion of the consciousness condition may include capability to normally respond to questions of a doctor or the like who conducted the inspection. The criterion of the kinesiological condition may include absence of big difference in kinesiological condition between before and after the inspection. The criterion of the audiovisual condition may include absence of big difference in audiovisual condition between before and after the inspection. These pieces of subject's condition criterion information are registered in advance in the database 51 shown in FIG. 2.

After the actual subject's condition information after the inspection and the subject's condition criterion information have been inputted, these pieces of information are compared with each other (S18). Here, there is difference between kinesiological conditions shown in FIGS. 10 and 11. A slightly dizzy condition was recognized after the inspection, but did not meet the criterion of big difference in kinesiological condition between before and after the inspection. In this case, a message indicating presence of biological condition difference data 65 (see FIG. 3) is displayed and a reason for the difference is selected or described (S20). That is, a reason why there was difference in kinesiological condition is inputted in accordance with necessity. Inputting the difference reason in this case can be carried out by selectively designating one from a plurality of prepared reasons or by direct inputting the reason, in the same manner as described above. FIG. 12 shows information with such difference by way of example. In FIG. 12, the kinesiological condition does not meet the criterion. With respect to this point, description has been made that the dose of the medicine C was so large (a dose of 4 ml was used while the normal dose is 2 ml) that the conditions of the subject should be observed continuously. These pieces of information are displayed on the display 35 and can be checked easily. That is, difference from the conditions after the general adequate medical inspection can be grasped quickly and accurately.

In the case where a reason is described for difference between the actual subject's condition information and the subject's condition criterion information as described above or in the case where there is no difference therebetween, an inspection certificate is created (S21). FIG. 13 shows an example of the inspection certificate.

The inspection certificate includes at least the actual use item information of the conducted medical inspection and the actual subject's condition information, in addition to the subject name, the inspection date, a pre-treatment staff in charge, an inspection doctor, and the type of the inspection. The actual use item information includes a used device, the type of a used endoscope, the unique number and washing history thereof, washing chemicals, washing condition, an indwelling needle, a pre-treatment medicine. By means of the inspection certificate, it is possible to easily and surely recognize whether the medical inspection was conducted properly or not, from information about presence/absence of conduction of predetermined events before and after the conducted medical inspection, difference between before and after the inspection and a reason for the difference. Although the inspection certificate can be outputted by the printer 39 shown in FIG. 2, any other output mode may be used. For example, the inspection certificate may be distributed as electronic data through the network or recorded on a recording medium 53 by the media drive device 45.

Incidentally, the medical inspection aid method is not limited to a method of checking records such as clinical records dated before the inspection and issuing an inspection certificate after conduction of the inspection, but may be conducted at any timing. For example, in conduction of the medical inspection, inspection propriety determination may be performed before a medical inspection practice is to be conducted and after a pre-treatment for the medical inspection has been conducted. On that occasion, actual use item information and adequate use item information in the pre-treatment are compared with each other so that whether difference therebetween is recognized or not or whether there is description of a reason for the difference is checked. When there is no difference or there is a reason for difference if the difference is present, the medical inspection is conducted. Otherwise, conduction of the medical inspection is cancelled. Checking presence/absence of the difference and the reason may be carried out by any method. For example, checking presence/absence of the difference and the reason can be carried out by the CPU 31 automatically by referring to the memory 33 (see FIG. 2). Presence/absence of the difference and the reason can be displayed, for example, on the display 35 so that a doctor, a nurse or the like can make judgment. Various kinds of information can be checked from the outside via the network. After conduction of the medical inspection, an inspection certificate including information of the inspection result is issued.

According to the medical inspection aid method in this case, a medical inspection is surely canceled when abnormality occurs in a pre-treatment in the case where the pre-treatment is required for the medical inspection. Thus, an inadequate medical inspection can be more surely prevented from being carried out by mistake.

In addition, when an inspection certificate is printed, the inspection certificate can be checked easily on a print not requiring a display medium.

Next, another example of the medical inspection aid method will be described.

There may be a contraindicated combination with a medical inspection due to a medical history or symptoms of a subject. Here, an example in which a medical inspection can be conducted in consideration of such contraindication information will be described.

FIG. 14 shows contraindicated combination information as contraindication information and alternative combination information. For example, buscopan (made by Nippon Boehring Ingelheim Co., Ltd., and containing scopolamine butylbramide as its main ingredient) is designated as a contraindicated medicine to a glaucomatous patient for a fear of increase in intraocular tension. The aforementioned buscopan is likewise designated as a contraindicated medicine also to a diabetic patent. For example, glucagon is designated as an alternative medicine to the contraindicated medicine. In this manner, since the medicine D shown in FIG. 14 is contraindicated to patents having different medical histories, information indicating that the medicine D should be replaced by a medicine E is collected for each type of inspection and every medical history.

As for information of the medical history and symptoms of the subject, subject's medical condition information may be prepared in advance as one of the input information in FIG. 3, though not shown. When difference information 29 is extracted, the adequate use item information described previously can be updated in accordance with necessity based on the subject's medical condition information and the contraindication information. FIG. 15 shows a result of the adequate use item information updated in consideration of the contraindication information. When the adequate use item information updated in consideration of the contraindication information and shown in FIG. 15 is compared with the adequate use item shown in FIG. 8, it can be known that the medicine D is changed to the medicine E and the dose of the medicine E is also changed.

When the adequate use item information in FIG. 15 is used in place of that in FIG. 8, a medical inspection in which a contraindicated combination with the medical history and symptoms of the subject can be avoided can be conducted more easily and surely. In this manner, in the embodiment, the control portion 15 serves as a contraindicated combination avoidance unit to implement a more adequate medical inspection.

According to the aforementioned medical inspection aid system 100, whether a medical inspection was conducted adequately or not can be recognized easily and surely from information about presence/absence of conduction of predetermined events before and after the medical inspection, difference between before and after the inspection and a reason for the difference. With an issued inspection certificate, the fact that the conducted medical inspection was carried out adequately can be certified and various kinds of information can be checked easily. As a result, a subject, subject's family or the like as well as a doctor or a nurse can be informed of the conduction contents and result of the medical inspection easily so that reliability of the medical inspection is improved.

Further, the inspection certificate may include information of things to pay attention to for the subject after the inspection, e.g. timing of dosing prescribed medicines including medicines taken orally, or restricted things in daily life. In that case, post-inspection reminder information 71 may be contained in advance in the database 51 as shown in FIG. 3 and adequately taken as descriptive data of the inspection certificate in accordance with the conducted medical inspection. In this manner, convenience of the inspection certificate for the subject can be enhanced.

What is claimed is:

1. A medical inspection aid system for determining whether a medical inspection conducted on a subject was carried out adequately or not, comprising:
an information input unit that inputs actual use item information and actual subject's condition information, the actual use item information including (i) information of at least one medical device used in a specific medical inspection conducted on a subject and (ii) information of at least one medical device and medicine used in a pre-treatment carried out on the subject prior to the specific medical inspection, the actual subject's condition information indicating biological conditions of the subject after conduction of the specific medical inspection; an information storage unit that stores the input information from the information input unit, adequate use item information and subject's condition criterion information, the adequate use item information including information of at least one normal medical device to be used in the medical inspection and at least one normal medical device and medicine to be used in the pre-treatment, the subject's condition criterion information indicating criteria for determining whether the biological conditions of the subject are normal or not after conduction of the medical inspection; a difference information extraction unit that compares the actual use item information with the adequate use item information and compares the actual subject's condition information with the subject's condition criterion information to thereby extract differences therebetween as difference information; and an adequacy determination unit that determines whether the conducted specific medical inspection was carried out adequately or not, based on the difference information.

2. The medical inspection aid system according to claim 1, wherein the difference information extraction unit compares the actual use item information with the adequate use item information to extract information of at least one medical device and medicine with differences therebetween, and registers the extracted information as use item difference data in the information storage unit, the difference information extraction unit also compares the actual subject's condition information with the subject's condition criterion information to thereby extract information of biological conditions where at least one of the actual subject's conditions fails to meet a corresponding one of the criteria, and registers the extracted information as biological condition difference data in the information storage unit, and when there is no registration of the difference information including the use item difference data and the biological condition difference data registered by the difference information extraction unit, the adequacy determination unit determines that the conducted specific medical inspection was conducted adequately.

3. The medical inspection aid system according to claim 2, wherein each of the actual use item information and the adequate use item information includes information of names of use items and quantities of the use items, and when difference in at least one of a name of each use item and a quantity of the use item is recognized between the actual use item information and the adequate use item information, data of the use item with the recognized difference are registered as use item difference data in the information storage unit.

4. The medical inspection aid system according to claim 2, further comprising: a difference reason adding unit that registers a reason for difference of the registered difference data in the information storage unit when one of the use item difference data and the biological condition difference data is registered in the information storage unit, wherein the adequacy determination unit removes difference data from the difference information when the reason is registered for the difference data by the difference reason adding unit.

5. The medical inspection aid system according to claim 1, further comprising: a contraindicated combination avoidance unit, wherein the information storage unit stores subject's medical condition information, contraindicated combination information and alternative combination information, the subject's medical condition information indicating disorders and symptoms of the subject, the contraindicated combination information indicating contraindicated combinations of the medical devices and the medicines with respect to the subject's medical condition information, the alternative combination information indicating alternative combinations for avoiding the contraindicated combinations, and when a contraindicated combination with the subject's medical condition information is found in the adequate use item information, the contraindicated combination avoidance unit changes the contraindicated combination to a corresponding one of the alternative combinations based on the contraindicated combination information and the alternative combination information.

6. The medical inspection aid system according to claim 1, wherein the information storage unit stores pieces of the adequate use item information and pieces of the subject's condition criterion information in accordance with a plurality of medical inspections respectively, and the difference information extraction unit selectively uses one piece of the adequate use item information and one piece of the subject's condition criterion information corresponding to the medical inspection conducted on the subject.

7. The medical inspection aid system according to claim 1, further comprising: an inspection certificate creation unit that creates an inspection certificate when the adequacy determination unit concludes that the conducted specific medical inspection was adequate.

8. The medical inspection aid system according to claim 7, wherein the inspection certificate includes at least the actual use item information and the actual subject's condition information corresponding to the specific medical inspection.

9. The medical inspection aid system according to claim 7, wherein the information storage unit stores post-inspection reminder information for the subject after conduction of the specific medical inspection, and the inspection certificate includes the post-inspection reminder information.

10. The medical inspection aid system according to claim 7, further comprising:
a print output unit that prints the inspection certificate.

11. The medical inspection aid system according to claim 1, further comprising:
a display unit that displays the difference information on a monitor screen together with any one of the information stored in the information storage unit.

12. A computer readable medium storing a program causing a computer to execute a process for a medical inspection aid method for determining whether a medical inspection conducted on a subject was carried out adequately or not, the process comprising:
determining adequate use item information and subject's condition criterion information in advance, the adequate use item information including information of at least one normal medical device to be used in a medical inspection and information of at least one normal medical device and medicine to be used in a pre-treatment to be conducted prior to the medical inspection, the subject's condition criterion information indicating criteria for determining whether biological conditions of the subject are normal or not after conduction of the medical inspection; inputting actual use item information and actual subject's condition information, the actual use item information including information of at least one medical device used in the specific medical inspection conducted on the subject and information of at least one medical device and medicine used in the pre-treatment, the actual subject's condition information indicating biological conditions of the subject after conduction of the specific medical inspection;
comparing the actual use item information with the adequate use item information and comparing the actual subject's condition information with the subject's condition criterion information to thereby extract differences therebetween as difference information; and
determining whether the conducted specific medical inspection was carried out adequately or not, based on the extracted difference information.

13. The computer readable medium according to claim 12, the process further comprising:
comparing the actual use item information with the adequate use item information to extract information of at least one medical device and medicine with differences therebetween, and registering the extracted information as use item difference data; comparing the actual subject's condition information with the subject's condition criterion information to thereby extract information of biological conditions where at least one of the actual subject's conditions fails to meet a corresponding one of the criteria, and registering the extracted information as biological condition difference data; and determining that the conducted specific medical inspection was carried out adequately when there is no registration of the difference information including the use item difference data and the biological condition difference data.

14. The computer readable medium according to claim 13, wherein each of the actual use item information and the adequate use item information includes information of names of use items and quantities of the use items, and when difference in at least one of a name of each use item and a quantity of the use item is recognized between the actual use item information and the adequate use item information, data of the use item with the recognized difference are registered as use item difference data.

15. The computer readable medium according to claim 13, the process further comprising:
removing difference data from the difference information registered as one of the use item difference data and the biological condition difference data when a reason of difference occurring in the difference data is registered for the difference data.

16. The computer readable medium according to claim 12, the process further comprising:
changing a contraindicated combination to a corresponding one of alternative combinations based on subject's medical condition information, contraindicated combination information and alternative combination information when the contraindicated combination with the subject's medical condition information is found in the adequate use item information, the subject's medical condition information indicating disorders and symptoms of the subject, the contraindicated combination information indicating contraindicated combinations of the medical devices and the medicines with respect to the subject's medical condition information, the alternative combination information indicating alternative combinations to the contraindicated combinations.

17. The computer readable medium according to claim 12, the process further comprising:
selectively using one piece of the adequate use item information and one piece of the subject's condition criterion information corresponding to the medical inspection conducted on the subject, from pieces of the adequate use item information and pieces of the subject's condition criterion information prepared in advance in accordance with a plurality of types of medical inspections.

18. The computer readable medium according to claim 12, the process further comprising: creating an inspection certificate when it is concluded that the conducted specific medical inspection was adequate.

19. The computer readable medium according to claim 18, wherein the inspection certificate includes at least the actual use item information and the actual subject's condition information corresponding to the conducted specific medical inspection.

20. The computer readable medium according to claim 18, wherein the inspection certificate includes post-inspection reminder information for the subject after conduction of the specific medical inspection.

21. The computer readable medium according to claim 18, the process further comprising:
printing out the inspection certificate after the inspection certificate is created.

22. The computer readable medium according to claim 12, the process further comprising:
displaying the difference information on a monitor screen together with at least one of the actual use item information and the actual subject's condition information.

* * * * *